United States Patent
Binder

(10) Patent No.: US 10,815,041 B2
(45) Date of Patent: Oct. 27, 2020

(54) SELECTIVELY OPENING MULTIPLE COMPARTMENT PACKAGES AND METHODS FOR MAKING SELECTIVELY OPENING MULTIPLE COMPARTMENT PACKAGES

(71) Applicant: Arye Binder, Brooklyn, NY (US)

(72) Inventor: Arye Binder, Brooklyn, NY (US)

( * ) Notice: Subject to any disclaimer, the term of this patent is extended or adjusted under 35 U.S.C. 154(b) by 21 days.

(21) Appl. No.: 15/820,986

(22) Filed: Nov. 22, 2017

(65) Prior Publication Data
US 2019/0152667 A1    May 23, 2019

(51) Int. Cl.
| | |
|---|---|
| *B65D 75/32* | (2006.01) |
| *B65D 81/32* | (2006.01) |
| *B65D 21/02* | (2006.01) |
| *B65D 33/16* | (2006.01) |
| *B65D 30/22* | (2006.01) |
| *A61F 6/04* | (2006.01) |
| *A61F 6/00* | (2006.01) |

(52) U.S. Cl.
CPC ....... *B65D 75/327* (2013.01); *B65D 21/0227* (2013.01); *B65D 31/12* (2013.01); *B65D 33/1691* (2013.01); *B65D 81/3261* (2013.01); *A61F 6/005* (2013.01); *A61F 6/04* (2013.01)

(58) Field of Classification Search
CPC .. B65D 75/327; B65D 21/0227; B65D 31/12; B65D 33/1691; B65D 81/3261; A61F 6/005; A61F 6/04
USPC .............................. 206/219, 538; 383/38–40
See application file for complete search history.

(56) References Cited

U.S. PATENT DOCUMENTS

| | | | |
|---|---|---|---|
| 2,339,283 A | 1/1944 | Mendel | |
| 2,391,094 A | 12/1945 | Karg | |
| 2,805,814 A | 9/1957 | Calasibetta et al. | |
| (Continued) | | | |

FOREIGN PATENT DOCUMENTS

| | | |
|---|---|---|
| CA | 2258877 | 7/2000 |
| CH | 693504 | 9/2003 |
| (Continued) | | |

OTHER PUBLICATIONS

"Trustex Natural Condom/Lube Combo," Global Protection Corp., globalprotection.com, retrieved at http://www.globalprotection.com/Merchant2/merchant.mvc?Screen=PROD&Product_Code=L8823LC on Aug. 10, 2017.
(Continued)

*Primary Examiner* — Chun Hoi Cheung
(74) *Attorney, Agent, or Firm* — Hartman & Citrin LLC

(57) ABSTRACT

Concepts and technologies disclosed herein for selectively opening multiple compartment packages and methods for making selectively opening multiple compartment packages. The selectively opening multiple compartment package can include a front layer having two sides; a second layer having two sides; a third layer having two sides; and a rear layer having two sides. Compartments of the selectively opening multiple compartment package can be formed and bound by a second side of the front layer and the first side of the second layer; a second side of the second layer and a first side of the third layer; and a second side of the third layer and a first side of the rear layer. The compartments are configured to be selectively opened.

14 Claims, 10 Drawing Sheets

(56) References Cited

U.S. PATENT DOCUMENTS

| | | | | |
|---|---|---|---|---|
| 3,255,872 | A * | 6/1966 | Shaw | B65D 81/3272 206/219 |
| 3,294,230 | A | 12/1966 | Penska | |
| 3,891,138 | A * | 6/1975 | Glas | B65D 31/12 206/219 |
| 4,201,031 | A | 5/1980 | Wiles | |
| 4,256,256 | A * | 3/1981 | Meyers | B65D 31/12 383/116 |
| 4,276,263 | A * | 6/1981 | Andersen | A01N 59/00 134/26 |
| 4,796,751 | A * | 1/1989 | Madkour | A47L 13/17 206/205 |
| 4,807,420 | A | 2/1989 | Barker | |
| 4,927,405 | A * | 5/1990 | Martin | B65D 31/12 206/569 |
| 5,005,695 | A | 4/1991 | Tennefos et al. | |
| 5,024,536 | A * | 6/1991 | Hill | B65D 31/12 383/38 |
| 5,111,934 | A * | 5/1992 | Morin | A47K 7/03 15/104.94 |
| D362,972 | S | 10/1995 | Wunsch | |
| 5,666,972 | A | 9/1997 | Gifford | |
| 5,881,883 | A * | 3/1999 | Siegelman | B65D 81/03 206/701 |
| 6,076,661 | A | 6/2000 | Abadi | |
| 6,234,675 | B1 * | 5/2001 | Saad | B65D 31/12 383/102 |
| 6,454,086 | B1 | 9/2002 | Bryson | |
| 6,662,530 | B1 * | 12/2003 | Millon | B65B 29/10 222/94 |
| 6,742,521 | B2 | 6/2004 | McCleskey et al. | |
| 7,204,368 | B2 * | 4/2007 | Cheaure | B65D 31/12 206/440 |
| 7,240,790 | B2 * | 7/2007 | Wendel | A45D 37/00 206/210 |
| D553,506 | S | 10/2007 | Parenteau | |
| 7,469,521 | B2 * | 12/2008 | Cheaure | B65D 31/12 53/412 |
| 8,302,776 | B2 * | 11/2012 | Lien | B65D 81/3261 206/370 |
| 8,534,461 | B2 | 9/2013 | Ludwig et al. | |
| 8,549,676 | B1 * | 10/2013 | Mandel | B65D 75/5805 4/245.1 |
| 9,248,045 | B2 | 2/2016 | Lee | |
| 2005/0045497 | A1 | 3/2005 | Sample | |
| 2012/0217237 | A1 | 8/2012 | Cole et al. | |
| 2015/0001106 | A1 | 1/2015 | Chopdat et al. | |
| 2016/0302962 | A1 | 10/2016 | Rivera et al. | |
| 2016/0374849 | A1 | 12/2016 | Nguyen et al. | |

FOREIGN PATENT DOCUMENTS

| | | |
|---|---|---|
| CN | 102784027 | 11/2012 |
| DE | 102007039837 | 2/2009 |
| EP | 3078357 | 10/2016 |
| FR | 2748995 | 11/1997 |
| GB | 2531617 | 9/2016 |
| JP | 2011-25944 | 2/2011 |
| WO | WO 95/02379 | 1/1995 |
| WO | WO 01/68473 | 9/2001 |
| WO | WO 2004/000682 | 12/2003 |

OTHER PUBLICATIONS

International Search Report and Written Opinion dated Jan. 28, 2019 in International Application No. PCT/US2018/062341.

* cited by examiner

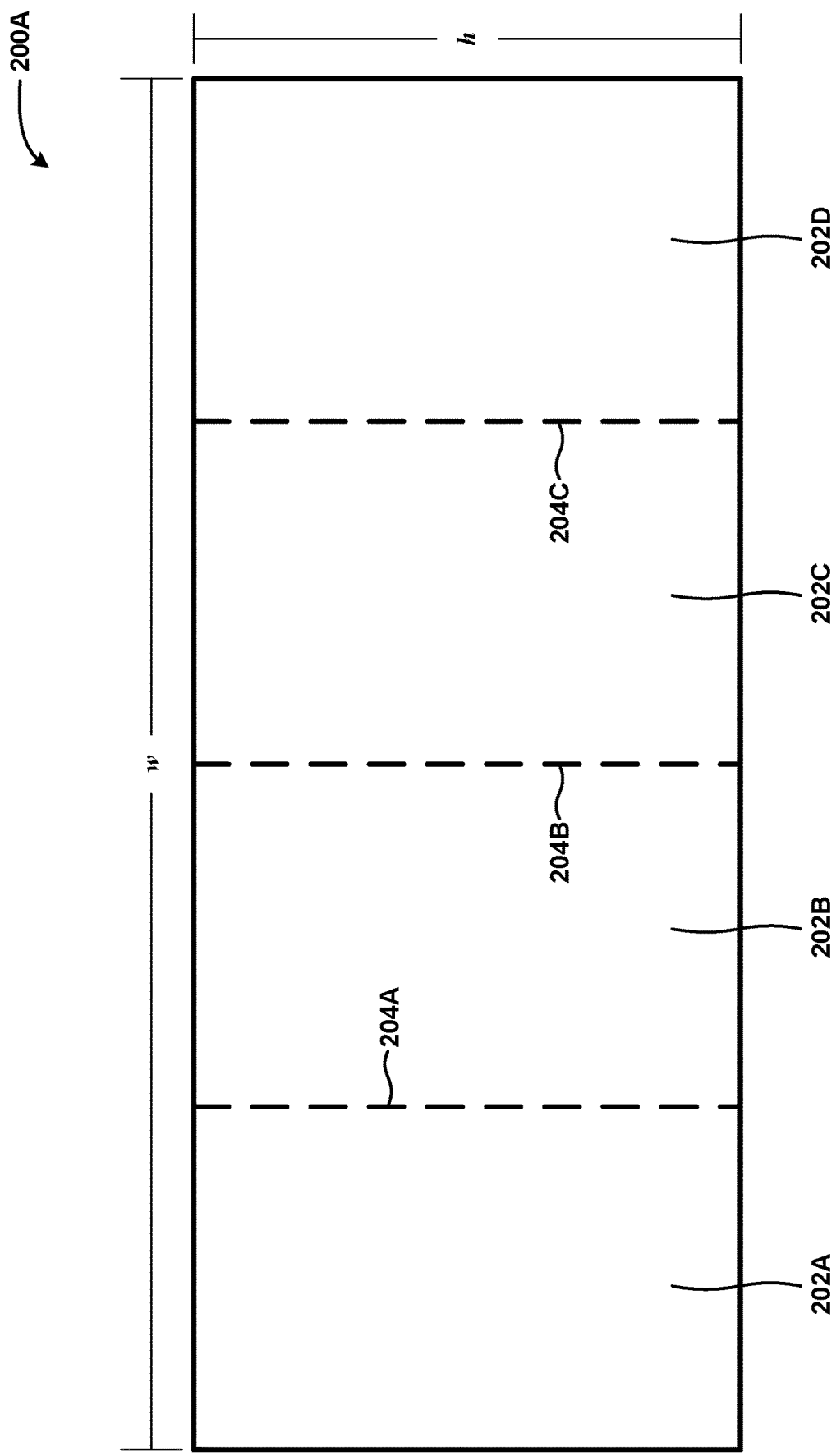

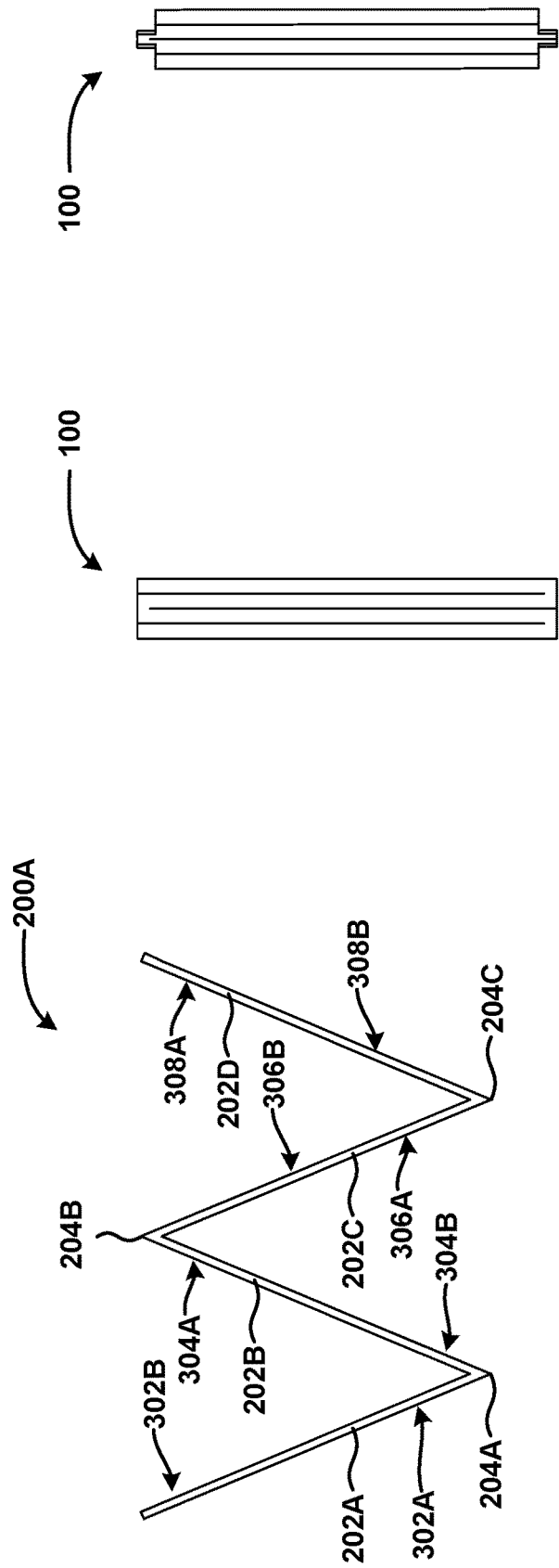

SELECTIVELY OPENING MULTIPLE COMPARTMENT PACKAGES AND METHODS FOR MAKING SELECTIVELY OPENING MULTIPLE COMPARTMENT PACKAGES

TECHNICAL FIELD

The present disclosure relates generally to packaging and, more particularly, to selectively opening multiple compartment packages and methods for making selectively opening multiple compartment packages.

BACKGROUND

Unless otherwise indicated herein, all disclosures in the background are not prior art to the claims in this application and are not admitted to be prior art by inclusion in this section.

Various types of goods are packaged for resale in packaging that is specifically tailored to the goods. In some instances, multiple items may be used in conjunction with one another, but may be manufactured by separate entities and/or may have their own dedicated packaging for various reasons. A user or other entity that wants to use multiple items may carry the items, in their dedicated packaging, for use. This approach can result in a large amount of waste and frustration for the user, in some cases.

SUMMARY

It should be appreciated that this summary is provided to introduce a selection of concepts associated with the concepts and technologies disclosed herein in a simplified form. The concepts discussed in this summary are further described below in the detailed description. This summary does not limit the scope of the claimed subject matter and/or the disclosure thereof in the detailed description and drawings in any way.

A blank of material can be obtained or formed with desired dimensions. The blank can be provided as a substantially planar unitary piece of material. In some embodiments, dimensions (width, height, and thickness) of the selectively opening multiple compartment package can be determined and a number of compartments to be included in the selectively opening multiple compartment package can also be determined. In some embodiments, the number of compartments can be based on how many items are to be stored in the selectively opening multiple compartment package (one item per compartment; two items per compartment; n items per compartment; combinations thereof; or the like). Based on these determinations, the dimensions of the blank can be determined (e.g., a width of the blank can be determined to be the number of compartments time the width of the selectively opening multiple compartment package). Because dimensions other than width can be used to determine dimensions of the blank, it should be understood that this example is illustrative, and therefore should not be construed as being limiting in any way.

The folded blank can be sealed on all but one edge, and the items to be stored by the selectively opening multiple compartment package can be disposed or otherwise located in the compartments formed by the folded material of the blank. The last edge of the blank can be sealed to form the selectively opening multiple compartment package. Various sealing techniques can be used to enable one or more compartments to be opened simultaneously. In some contemplated embodiments, each compartment can be opened separately. In some embodiments, the selectively opening multiple compartment package is separable into multiple single-compartment packages for convenience. It should be understood that this example is illustrative, and therefore should not be construed as being limiting in any way.

According to one aspect of the embodiments disclosed herein, a selectively opening multiple compartment package is disclosed. The selectively opening multiple compartment package can include a front layer. The front layer can include a first side of the front layer and a second side of the front layer. The selectively opening multiple compartment package further can include a first divider having a first side of the first divider and a second side of the second divider. The selectively opening multiple compartment package further can include a second divider having a first side of the second divider and a second side of the second divider. The selectively opening multiple compartment package further can include a rear layer having a first side of the rear layer and a second side of the rear layer. The selectively opening multiple compartment package further can include a first compartment bound by the second side of the front layer and the first side of the first divider; a second compartment bound by the second side of the first divider and the first side of the second divider; and a third compartment bound by the second side of the second divider and the first side of the rear layer. The first side of the front layer and the second side of the rear layer can include external surfaces of the selectively opening multiple compartment package, and the first compartment, the second compartment, and the third compartment can be configured to be selectively opened.

In some embodiments, the second side of the front layer and the first side of the first divider can be sealed together by a first seal. The second side of the first divider and the first side of the second divider can be sealed together by a second seal, and the second side of the second divider and the first side of the rear layer can be sealed together by a third seal. In some embodiments, selectively opening can include destroying one seal of the first seal, the second seal, or the third seal. In some embodiments, the front layer can be formed from a first panel of a material blank, the first divider can be formed from a second panel of the material blank, the second divider can be formed from a third panel of the material blank, and the rear layer can be formed from a fourth panel of the material blank.

In some embodiments, the material blank can be formed as a single piece of material that can be folded to form the panels. In some embodiments, the selectively opening multiple compartment package further can include a first item located in the first compartment, a second item that is different from the first item can be located in the second compartment, and a third item that is different from the first item and the second item can be located in the third compartment. In some embodiments, the selectively opening multiple compartment package can be formed from a single unitary piece of laminated foil that can be folded.

According to another aspect of the embodiments disclosed herein, a selectively opening multiple compartment package is disclosed. The selectively opening multiple compartment package can include a front layer. The front layer can include a first side of the front layer and a second side of the front layer. The selectively opening multiple compartment package further can include a first divider. The first divider can include a first side of the first divider and a second side of the second divider. The selectively opening multiple compartment package further can include a second divider. The second divider can include a first side of the second divider and a second side of the second divider. The selectively opening multiple compartment package further can include a rear layer. The rear layer can include a first side of the rear layer and a second side of the rear layer. The selectively opening multiple compartment package further can include a first compartment bound by the second side of the front layer and the first side of the first divider; a second compartment bound by the second side of the first divider and the first side of the second divider; and a third compartment bound by the second side of the second divider and the first side of the rear layer. The first side of the front layer and the second side of the rear layer can include external surfaces of the selectively opening multiple compartment package, and the second compartment can be opened without opening the first compartment and without opening the third compartment.

In some embodiments, the second side of the front layer and the first side of the first divider can be sealed together by a first seal. The second side of the first divider and the first side of the second divider can be sealed together by a second seal, and the second side of the second divider and the first side of the rear layer can be sealed together by a third seal. In some embodiments, selectively opening includes destroying the second seal. In some embodiments, the front layer can be formed from a first panel of a material blank. The first divider can be formed from a second panel of the material blank, the second divider can be formed from a third panel of the material blank, and the rear layer can be formed from a fourth panel of the material blank. In some embodiments, the material blank can be formed as a single piece of material that can be folded to form the panels.

In some embodiments, the selectively opening multiple compartment package further can include a first item located in the first compartment, a second item that can be different from the first item can be located in the second compartment, and a third item that can be different from the first item and the second item can be located in the third compartment. In some embodiments, the selectively opening multiple compartment package can be formed from a single unitary piece of laminated foil that can be folded. In some embodiments, the selectively opening multiple compartment package further can include a tear line. Tearing along the tear line enables separation of the first compartment from the second compartment and separation of the third compartment from the second compartment.

According to yet another aspect of the embodiments disclosed herein, a method is disclosed. The method can include obtaining, by a package forming machine including a processor, a material blank including a unitary and substantially planar piece of material; folding, by the package forming machine, the material blank along a first fold line; folding, by the package forming machine, the material blank along a second fold line; and folding, by the package forming machine, the material blank along a third fold line, whereby an unsealed package having four edges can be obtained. The method also can include sealing, by the package forming machine, three edges of the four edges; locating, by the package forming machine, a first item in a first compartment of the unsealed package; locating, by the package forming machine, a second item in a second compartment of the unsealed package; locating, by the package forming machine, a third item in a third compartment of the unsealed package; and sealing, by the package forming machine, a fourth edge of the four edges to seal the first compartment, the second compartment, and the third compartment, whereby a selectively opening multiple compartment package can be formed.

In some embodiments, the method further can include sealing, by the package forming machine, the material blank after folding along the second fold line and before folding along the third fold line, whereby the first compartment can be formed by the sealing and whereby the third compartment can be formed by the sealing. In some embodiments, the second compartment can be formed by sealing the three edges. In some embodiments, the method further can include forming, by the package forming machine, perforations in the material blank. The selectively opening multiple compartment package can include a tear line, whereby the selectively opening multiple compartment package can be separated into single compartment packages by tearing along the tear line. In some embodiments, the method further can include forming, by the package forming machine, perforations in the selectively opening multiple compartment package, whereby the selectively opening multiple compartment package can be separated into single compartment packages by tearing along the perforations.

The features, functions, and advantages discussed herein can be achieved independently in various embodiments of the concepts and technologies disclosed herein, or may be combined in yet other embodiments, further details of which can be seen with reference to the following description and drawings. As noted above, the foregoing summary is illustrative only and is not limiting in any way. In addition to the illustrative aspects, embodiments, and features described above, further aspects, embodiments, and features will become apparent by reference to the drawings and the following detailed description.

BRIEF DESCRIPTION OF THE DRAWINGS

FIG. 2A is a line drawing showing a front elevation view of a material blank that can be used to form a selectively opening multiple compartment package, according to an illustrative embodiment of the concepts and technologies disclosed herein.

FIGS. 3A-3G are line drawings that schematically illustrate forming the selectively opening multiple compartment package from a material blank, according to some example embodiments of the concepts and technologies disclosed herein.

DETAILED DESCRIPTION

Figure 1A:
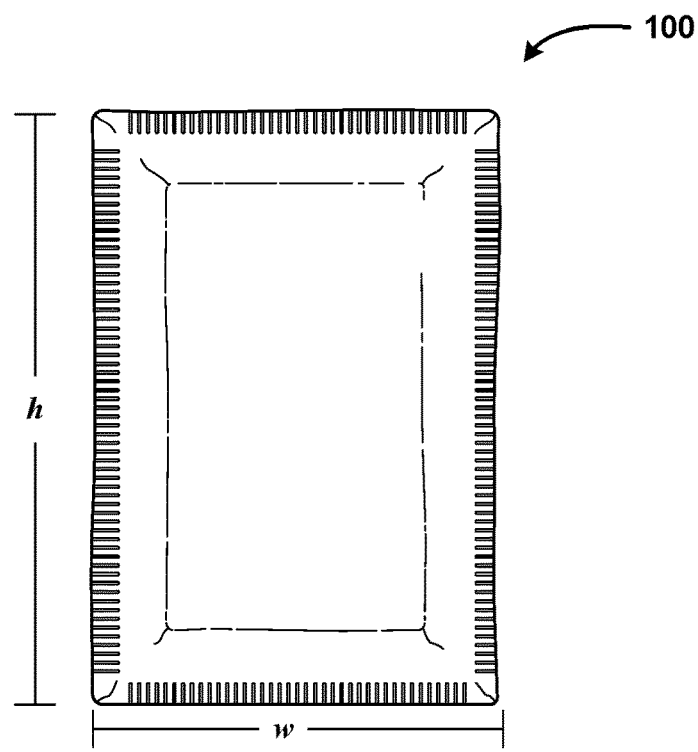
FIG. 1A is a line drawing showing a front elevation view of a selectively opening multiple compartment package, according to some illustrative embodiments of the concepts and technologies disclosed herein.

The following detailed description is directed to selectively opening multiple compartment packages and methods for making selectively opening multiple compartment packages. A blank of material can be obtained or formed with desired dimensions. In some embodiments, dimensions (width, height, and thickness) of the selectively opening multiple compartment package can be determined and a number of compartments to be included in the selectively opening multiple compartment package can also be determined. In some embodiments, the number of compartments can be based on how many items are to be stored in the selectively opening multiple compartment package (one item per compartment; two items per compartment; n items per compartment; combinations thereof; or the like). Based on these determinations, the dimensions of the blank can be determined (e.g., a width of the blank can be determined to be the number of compartments times the width of the selectively opening multiple compartment package). Because dimensions other than width can be used to determine dimensions of the blank, it should be understood that this example is illustrative, and therefore should not be construed as being limiting in any way.

The folded blank can be sealed on all but one edge, and the items to be stored by the selectively opening multiple compartment package can be disposed or otherwise located in the compartments formed by the folded material of the blank. The last edge of the blank can be sealed to form the selectively opening multiple compartment package. Various sealing techniques can be used to enable one or more compartments to be opened simultaneously. In some contemplated embodiments, each compartment can be opened separately. In some embodiments, the selectively opening multiple compartment package is separable into multiple single-compartment packages for convenience. It should be understood that this example is illustrative, and therefore should not be construed as being limiting in any way. These and other advantages and features will become apparent from the description of the various embodiments below.

In the following detailed description, references are made to the accompanying drawings that form a part hereof and that show, by way of illustration, specific embodiments or examples. It must be understood that the disclosed embodiments are merely illustrative of the concepts and technologies disclosed herein. The concepts and technologies disclosed herein may be embodied in various and alternative forms, and/or in various combinations of the embodiments disclosed herein. The word "illustrative," as used in the specification, is used expansively to refer to embodiments that serve as an illustration, specimen, model or pattern.

Additionally, it should be understood that the drawings are not necessarily to scale, and that some features may be exaggerated or minimized to show details of particular components. In other instances, well-known components, systems, materials or methods have not been described in detail in order to avoid obscuring the present disclosure. Therefore, specific structural and functional details disclosed herein are not to be interpreted as limiting, but merely as a basis for the claims and as a representative basis for teaching one skilled in the art to variously employ the present disclosure. Referring now to the drawings, in which like numerals represent like elements throughout the several figures, aspects of selectively opening multiple compartment packages and methods for making selectively opening multiple compartment packages will be described.

Referring now to FIG. 1A, some aspects of selectively opening multiple compartment packages according to various embodiments of the concepts and technologies disclosed herein will be described in detail. In particular, FIG. 1A illustrates a selectively opening multiple compartment package 100 according to one example embodiment of the concepts and technologies disclosed herein. As shown in FIG. 1A, the selectively opening multiple compartment package 100 can appear, from the exterior, as a single compartment package. The selectively opening multiple compartment package 100 is shown as having a substantially rectangular profile (e.g., a front elevation view of the selectively opening multiple compartment package 100 such as that illustrated in FIG. 1A can have a height h that is greater than its width w).

Also, although not labeled in FIG. 1A, the selectively opening multiple compartment package 100 has a thickness t that extends toward or away from a viewpoint associated with FIG. 1A, and the thickness is not necessarily (and in fact most likely is not) consistent. The thickness(es) of the selectively opening multiple compartment package 100 are more easily seen in FIG. 1B. It should be understood that the illustrated example is illustrative, and therefore should not be construed as being limiting in any way. In particular, the selectively opening multiple compartment package 100 can have a substantially square profile and/or can be formed having other shapes and/or profiles without departing from the various embodiments of the concepts and technologies disclosed herein. Furthermore, ratios and/or relationships between the height, width, and thickness(es) of the selectively opening multiple compartment package 100 are illustrative only and should not be construed as being limiting in any way.

Figure 1B:
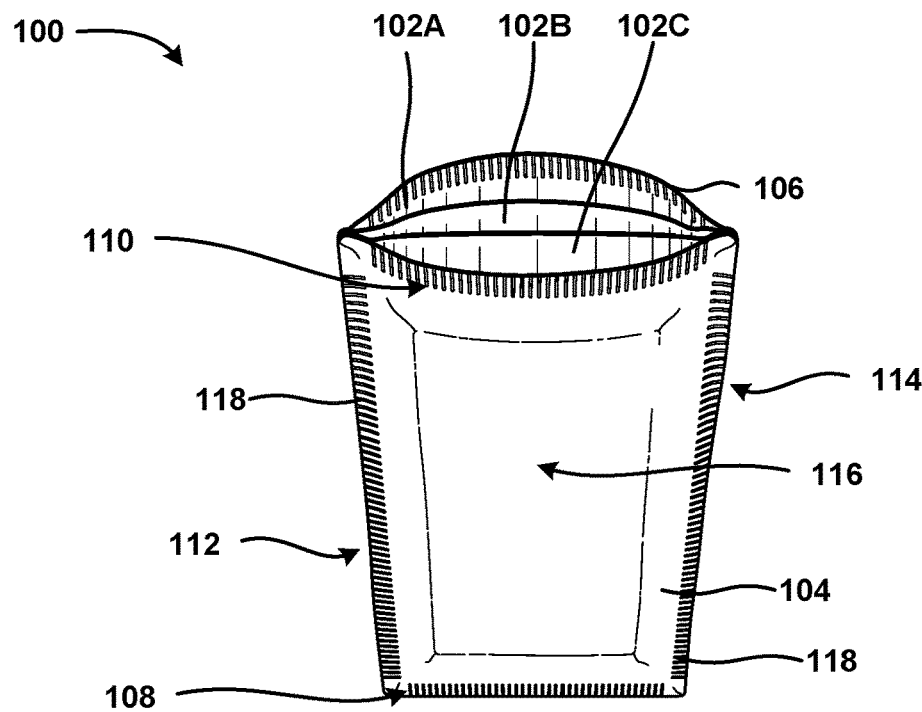
FIG. 1B is a line drawing showing a perspective view of the selectively opening multiple compartment package after exposing the compartments thereof, according to some illustrative embodiments of the concepts and technologies disclosed herein.

With additional reference now to FIG. 1B, additional aspects of the selectively opening multiple compartment package 100 will be described. In particular, FIG. 1B is a line drawing illustrating the selectively opening multiple compartment package 100 shown in FIG. 1A after opening or otherwise separating the multiple layers thereof. In the illustrated embodiment shown in FIG. 1B, the selectively opening multiple compartment package 100 includes a first compartment 102A, a second compartment 102B, and a third compartment 102C (hereinafter collectively and/or generically referred to as "compartments 102"). It should be understood that this example is illustrative, and therefore should not be construed as being limiting in any way. It should be understood that the designation of the first, second, and third of the compartments 102 of the selectively opening multiple compartment package 100 is merely for reference and for purposes of describing the concepts and technologies disclosed herein. Thus, the numerical designation of the compartments 102 does not indicate importance or otherwise provide any differentiation among the compartments 102 illustrated and described herein. Furthermore, it should be understood that in some embodiments of the selectively opening multiple compartment package 100, more than three compartments 102 can be included. The three-compartment embodiment of the selectively opening multiple compartment package 100 is illustrated and described herein for purposes of simplifying the description herein.

In the illustrated embodiment, the selectively opening multiple compartment package 100 is used to store three items. According to various embodiments, each one of the three items can be placed into a one of the three compartments 102 of the selectively opening multiple compartment package 100. For example, a first item (not visible in FIG. 1B) can be located in the first compartment 102A of the selectively opening multiple compartment package 100, a second item (not visible in FIG. 1B) can be located in the second compartment 102B of the selectively opening multiple compartment package 100, and a third item (not visible in FIG. 1B) can be located in the third compartment 102C of the selectively opening multiple compartment package 100. Because the three or more items can be located in three or more compartments 102 of the selectively opening multiple compartment package 100 in various manners, it should be understood that this example is illustrative, and therefore should not be construed as being limiting in any way.

According to various embodiments, each of the compartments 102 of the selectively opening multiple compartment package 100 can be hermetically sealed. The hermetic sealing of the compartments 102 of the selectively opening multiple compartment package 100 can be used to protect and/or separate each of the three items stored by the selectively opening multiple compartment package 100. In some embodiments of the concepts and technologies disclosed herein, the three compartments 102 of the selectively opening multiple compartment package 100 can be sealed such that each of the three compartments 102 can be separately and selectively opened (or not opened). Thus, for example, a user or other entity can open the second compartment 102B of the selectively opening multiple compartment package 100 without opening the first compartment 102A and/or the third compartment 102C of the selectively opening multiple compartment package 100. It therefore can be understood that a particular item of the three items can be accessed by opening a corresponding one of the compartments 102 of the selectively opening multiple compartment package 100 without accessing the other two items, if desired.

In some embodiments, as will be illustrated and described in more detail below with reference at least to FIG. 1B, some embodiments of the selectively opening multiple compartment package 100 can be configured such that two of the compartments 102 of the selectively opening multiple compartment package 100 can be configured such that the first compartment 102A can be separable from the selectively opening multiple compartment package 100 and can function as a first package (with a single compartment 102); and the third compartment 102C can be separable from the selectively opening multiple compartment package 100 and can function as a second package (with a single compartment 102). Some embodiments of a separable version of the selectively opening multiple compartment package 100 will be illustrated and described in more detail hereinbelow.

In some other embodiments, the selectively opening multiple compartment package 100 can be intended for one use (of all three items). Thus, in some embodiments, any unopened compartments 102 of the selectively opening multiple compartment package 100 can be left unopened when the selectively opening multiple compartment package 100 is discarded. It should be understood that this example is illustrative, and therefore should not be construed as being limiting in any way.

In some contemplated embodiments of the selectively opening multiple compartment package 100, the first compartment 102A can store a first item and the second and third compartments 102B, 102C can store supplementary items that may or may not be related to the item in the first compartment 102. In some contemplated embodiments, one of the compartments 102 can store a condom such as, for example, a male condom or a female condom, and two of the compartments 102 can store items that are related to, supplemental to, complementary to, and/or otherwise may relate in some way to the condom. For example, each of the two compartments 102B, 102C may store one or more items such as, a wipe (e.g., a baby wipe, a wet wipe, a napkin, or the like); a lubricant or lubricating material; one or more medications (e.g., birth control pills, vasodilators, emergency contraceptive pills, or the like); one or more herbal supplements; gloves; creams; oils; spermicide; contraceptive films; other items; or the like.

According to various embodiments of the concepts and technologies disclosed herein, a particular one of the compartments 102 of the selectively opening multiple compartment package 100 may store multiple items. According to some other embodiments, an item similar to an item stored in one of the compartments 102 of the selectively opening multiple compartment package 100 is not stored in another of the compartments 102 of the selectively opening multiple compartment package 100. Thus, each of the compartments 102 of the selectively opening multiple compartment package 100 can store a different item and/or items (relative to the other compartments 102 of the selectively opening multiple compartment package 100). It should be understood that this example is illustrative, and therefore should not be construed as being limiting in any way.

As shown in FIG. 1B, the selectively opening multiple compartment package 100 can have a front surface 104, a rear surface 106, a bottom edge 108, a top edge 110, a first side edge 112, a second side edge 114, a center area 116, and sealed portions 118. Of course, it can be appreciated that the various edges (i.e., the bottom edge 108, the top edge 110, the first side edge 112, and the second side edge 114) can be reversed and/or interchanged. The designation of these edges is purely conventional and these terms are introduced to aid in the description of the illustrated embodiments of the concepts and technologies disclosed herein. As such, these designations are not used to limit the embodiments of the concepts and technologies disclosed herein in any way.

As shown in FIG. 1B, the selectively opening multiple compartment package 100 can include multiple sealed portions 118. The sealed portions 118 can be formed from the same materials as unsealed portions of the selectively opening multiple compartment package 100, according to various embodiments, though chemical adhesives can be applied to the materials, in some embodiments, to form the sealed portions 118. In some other embodiments, the sealed portions 118 can be formed from the same materials as the unsealed portions, and heat, pressure, compression, and/or other mechanical manipulations of the materials may be completed to form the sealed portions 118. The creation of the sealed portions 118 will be more clearly understood with additional reference to the other FIGURES and the descriptions thereof found hereinbelow.

As can be seen in FIG. 1B, selectively opening multiple compartment package 100 can be opened to reveal the multiple compartments 102. As shown in FIG. 1B, the selectively opening multiple compartment package 100 has been opened such that all of the compartments 102 are accessible. Each of the compartments 102, however, can be selectively and separately opened. As such, at various times and/or in various implementations of the selectively opening multiple compartment package 100, zero compartments 102 may be opened; one compartment 102 may be opened; two compartments may be opened; three compartments may be opened; and/or more than three (if the selectively opening multiple compartment package 100 is so equipped) may be opened. As such, the illustrated embodiment must be understood as being illustrative and should not be construed as being limiting in any way.

As can be appreciated with reference to FIGS. 1A-1B, a thickness of the selectively opening multiple compartment package 100 can vary at various points or locations of the selectively opening multiple compartment package 100. In particular, the selectively opening multiple compartment package 100 can have a first thickness at a sealed portion 118 (e.g., near the one of the side edges 112) and can have a second thickness at an unsealed portion (e.g., the center 116) of the selectively opening multiple compartment package 100. The thickness of the selectively opening multiple compartment package 100 is more easily appreciated with reference to FIG. 4 below. It should be understood that this example is illustrative, and therefore should not be construed as being limiting in any way.

Turning now to FIG. 2A, additional aspects of the selectively opening multiple compartment package 100 will be described in detail. In particular, FIG. 2A is a line drawing showing a front elevation view of a material blank (hereinafter referred to as a "blank") 200A that can be used to form the selectively opening multiple compartment package 100, according to an illustrative embodiment of the concepts and technologies disclosed herein. The blank 200A (and other blanks that can be used in accordance with the concepts and technologies disclosed herein) can be formed as a single unitary piece that is folded to form the structures illustrated and described herein. The blank 200A can include a piece of a material from which the selectively opening multiple compartment package 100 is to be formed. According to various embodiments, the blank 200A can be formed from one or more materials including, but not limited to, metal foils; laminated metal foils; papers; foil-lined, wax-lined, and/or laminated papers; plastics or other polymers; wax-lined or foil-lined papers or polymers; other materials; combinations thereof; or the like.

The dimensions of the blank 200A, including the width w, the height h, and the thickness t can be selected based on the desired dimensions of the selectively opening multiple compartment package 100. In the illustrated embodiment shown in FIG. 2A, the width w can be determined based on the desired width of the selectively opening multiple compartment package 100, namely the width w of the blank 200A can be four times the desired width of the selectively opening multiple compartment package 100. It should be understood that this example is illustrative, and therefore should not be construed as being limiting in any way.

As shown in FIG. 2A, the blank 200A can include four panels 202A-D (hereinafter collectively and/or generically referred to as "panels 202"). The four panels 202 shown in FIG. 2A can be configured to provide side walls of the three compartments 102 as described with respect to the selectively opening multiple compartment package 100 shown in FIGS. 1A-1B. As explained above with reference to FIGS. 1A-1B, the selectively opening multiple compartment package 100 can be formed with more than three compartments 102, and as such, the blank 200A (or other blanks in accordance with various embodiments of the concepts and technologies disclosed herein) can be formed with more than four panels 202.

With collective reference to FIGS. 1A-2A, it can be appreciated that one side of the panel 202A (e.g., the surface facing the viewing plane in FIG. 2A) can provide one of the front surface 104 of the selectively opening multiple compartment package 100. The blank 200A can be folded (e.g., at a first location as shown by the fold line 204A in FIG. 2A) and the first compartment 102A can be formed thereby. Thus, it can be appreciated that the first compartment 102A can be bound by the panels 202A and 202B. Similarly, the blank 200A can again be folded (e.g., at a second location as shown by the fold line 204B in FIG. 2A) and the second compartment 102B can be formed thereby. Thus, the second compartment 102B can be bound by the panels 202B and 202C. The blank 200A can yet again be folded (e.g., at a third location as shown by the fold line 204C in FIG. 2A) and the third compartment 102C can be formed thereby. Therefore, the third compartment 102C can be formed thereby, and can be bound by the panels 202C and 202D. It should be understood that this example is illustrative, and therefore should not be construed as being limiting in any way.

In some embodiments, the selectively opening multiple compartment package 100 can be formed by way of the folds illustrated and described herein, as well as sealing of the panels 202. According to various embodiments, the panels 202 can be sealed using heat, glue, mechanical compression and/or manipulation, combinations thereof, or the like. In one contemplated embodiment, the panels 202 can be folded as explained above, and the panels 202 can be sealed on three sides (e.g., along the width w at the bottom edge 108; and along the side edges 112, 114), thereby forming the compartments 102. The items for packaging in the selectively opening multiple compartment package 100 can be placed, disposed, or otherwise located in the compartments 102. The fourth side of the panels 202 can be sealed (e.g., along the width w at the top edge 110). The method of sealing the panels 202 can be selected such that the panels 202 can be peeled (at least partially) from one another, thereby opening and/or otherwise enabling access to the items within the compartments 102. In some contemplated embodiments, different types of sealing can be used. For example, three sides of the panels 202 can be sealed using a first type of sealing (e.g., mechanical, heat, chemical adhesive, etc.) and the fourth side of the panels 202 can be sealed using a second type of sealing. It should be understood that this example is illustrative, and therefore should not be construed as being limiting in any way.

It should be understood that additional and/or other materials can be applied to the selectively opening multiple compartment package 100 and/or the blank 200A (before or after folding). For example, in some embodiments, the selectively opening multiple compartment package 100 can have one or more surfaces lined with antifungal compounds, antibacterial compounds, scents and/or flavorings, preservatives, other materials, combinations thereof, or the like. Because additional and/or alternative materials can be applied to the blank 200A and/or the selectively opening multiple compartment package 100, it should be understood that these examples are illustrative, and therefore should not be construed as being limiting in any way.

Figure 2B:
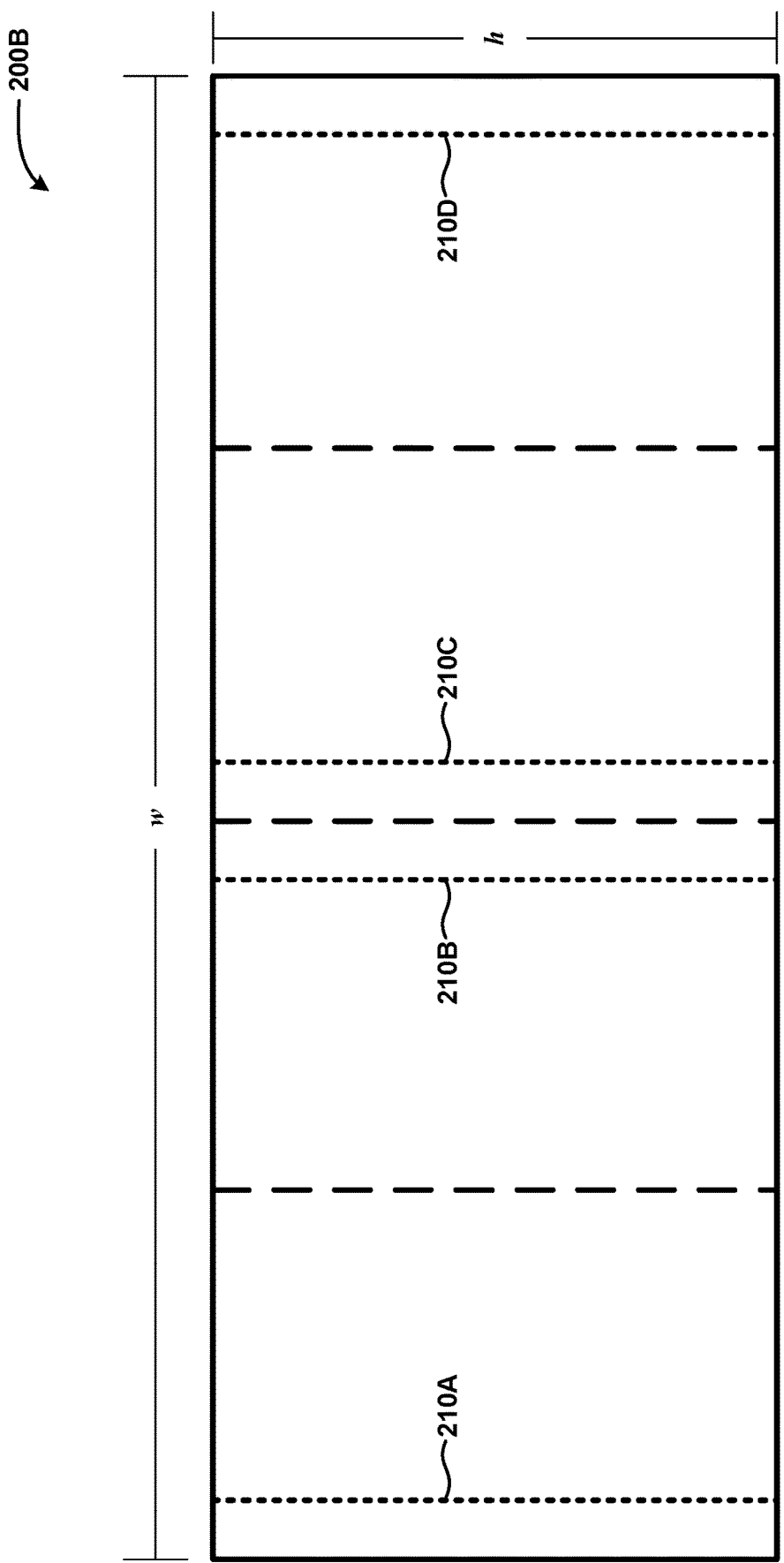
FIG. 2B is a line drawing showing a front elevation view of a material blank that can be used to form a selectively opening multiple compartment package, according to another illustrative embodiment of the concepts and technologies disclosed herein.

Turning now to FIG. 2B, additional aspects of the selectively opening multiple compartment package 100 will be described in detail. In particular, FIG. 2B is a line drawing showing a front elevation view of a material blank (hereinafter collectively and/or generically referred to as a "blank") 200B that can be used to form a selectively opening multiple compartment package 100, according to another illustrative embodiment of the concepts and technologies disclosed herein. The blank 200B can include a piece of a material from which the selectively opening multiple compartment package 100 is to be formed. According to various embodiments, the blank 200B can be formed from one or more materials as explained above with respect to the blank 200A. The dimensions of the blank 200B also can be selected based on the desired dimensions of the selectively opening multiple compartment package 100, as explained above. The blank 200B also is illustrated as including four panels 202. As explained above, the blank 200B can be formed with more than four panels 202. It can be appreciated that the compartments 102 can be formed by the panels 202 as folded along the fold lines 204. The blank 200B also can include perforations 210A-D (hereinafter collectively and/or generically referred to as "perforations 210"). In some embodiments, the perforations 210 can be omitted from the blank 200B (in which case the blank 200B can be substantially similar to the blank 200A) and instead can be created in the selectively opening multiple compartment package 100 during the folding operations illustrated and described hereinbelow with reference to FIGS. 3A-3E. The blank 200B will be described as including the perforations 210, but this embodiment should be understood as being illustrative, and therefore should not be construed as being limiting in any way.

In some embodiments, the selectively opening multiple compartment package 100 can be formed by way of folding the blank 200B and by way of sealing the panels 202. The panels 202 of the blank 200B can be sealed using heat, glue, mechanical compression and/or manipulation, combinations thereof, or the like. In one contemplated embodiment, the selectively opening multiple compartment package 100 can be formed by folding the panels 202 as explained above, and the panels 202 can be sealed on three sides (e.g., along the width w at the bottom edge 108; and along the side edges 112, 114), thereby forming the compartments 102. The items for packaging in the selectively opening multiple compartment package 100 can be placed, disposed, or otherwise located in the compartments 102. The fourth side of the panels 202 can be sealed (e.g., along the width w at the top edge 110). The method of sealing the panels 202 can be selected such that the panels 202 can be peeled (at least partially) from one another, thereby opening and/or otherwise enabling access to the items within the compartments 102. In some contemplated embodiments, different types of sealing can be used. For example, three sides of the panels 202 can be sealed using a first type of sealing (e.g., mechanical, heat, chemical adhesive, etc.) and the fourth side of the panels 202 can be sealed using a second type of sealing. It should be understood that this example is illustrative, and therefore should not be construed as being limiting in any way.

Figure 3D:
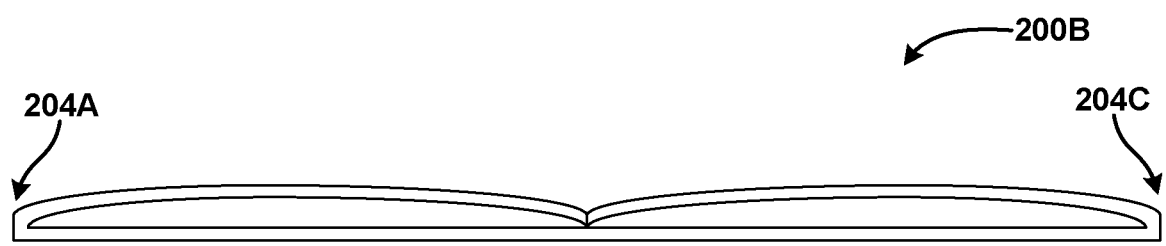

Turning now to FIGS. 3A-3G, additional aspects of the selectively opening multiple compartment package 100 will be described in detail. In particular, FIGS. 3A-3C schematically illustrate various aspects of the folding operations illustrated and described above with reference to FIG. 2A. It should be understood that this example is illustrative, and therefore should not be construed as being limiting in any way.

Figure 4A:
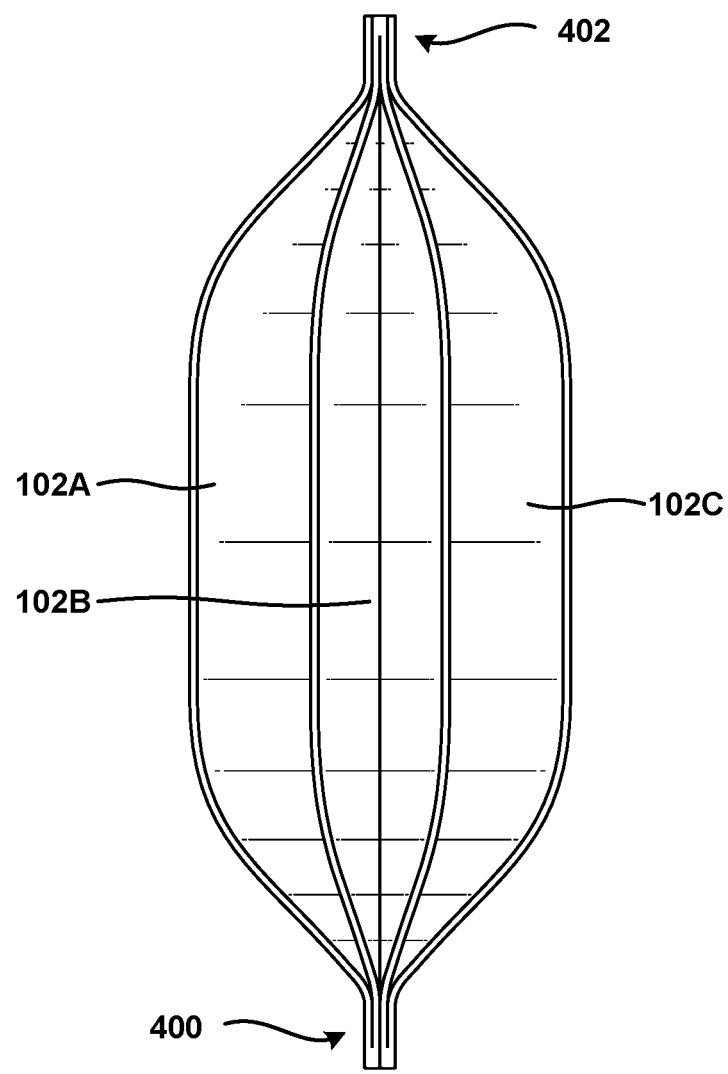
FIG. 4A is a line drawing showing a top elevation view of a selectively opening multiple compartment package, according to some illustrative embodiments of the concepts and technologies disclosed herein.

As shown in FIG. 3A, the blank 200A can be folded at least at three locations. In some embodiments, as shown in FIG. 3A, the blank 200A can be folded at three locations that can correspond to the fold lines 204. After collapsing the blank 200A by folding as shown in FIG. 3A, the selectively opening multiple compartment package 100 can be obtained, as shown in FIG. 3B. In some embodiments, a compression seal, a heat seal, an adhesive, or other sealing mechanism(s) can be used to crimp or seal some or all edges of the selectively opening multiple compartment package 100 as shown in FIG. 3C. A top view of the selectively opening multiple compartment package 100 is shown in FIG. 4A and will be illustrated and described in more detail below with reference thereto. It should be understood that this example is illustrative, and therefore should not be construed as being limiting in any way.

Figure 3E:
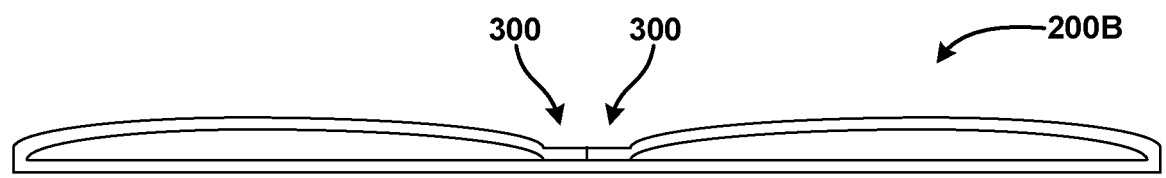

FIGS. 3D-3G schematically illustrate various aspects of the folding operations illustrated and described above with reference to FIG. 2B. It should be understood that this example is illustrative, and therefore should not be construed as being limiting in any way. As shown in FIG. 3D, the blank 200B can be folded at least at three locations. In the illustrated embodiment, as shown in FIG. 3D, the blank 200B can be folded at two locations that can correspond to the fold lines 204A and 204C. After collapsing the blank 200B by folding along the two fold lines 204A and 204C as shown in FIG. 3D, a crimp, adhesive, heat, or other seal ("compartment seal") 300 can be applied to the folded blank 200B to create two of the compartments 102, as shown in FIG. 3E. It therefore can be appreciated that the folded blank 200B can have two compartments 102, though these are not labeled in FIG. 3E.

Figure 3F:
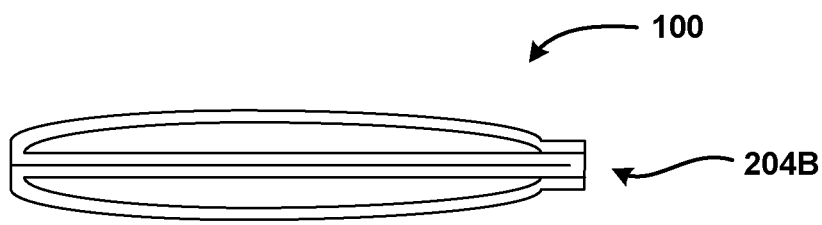
Figure 3G:
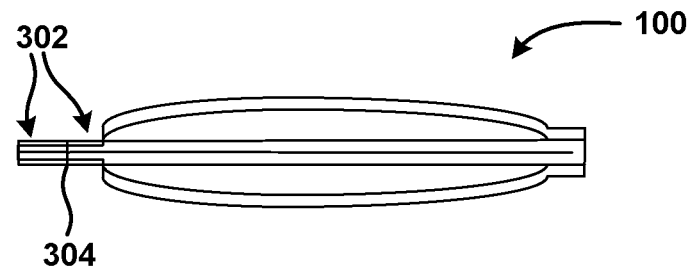
Figure 4B:
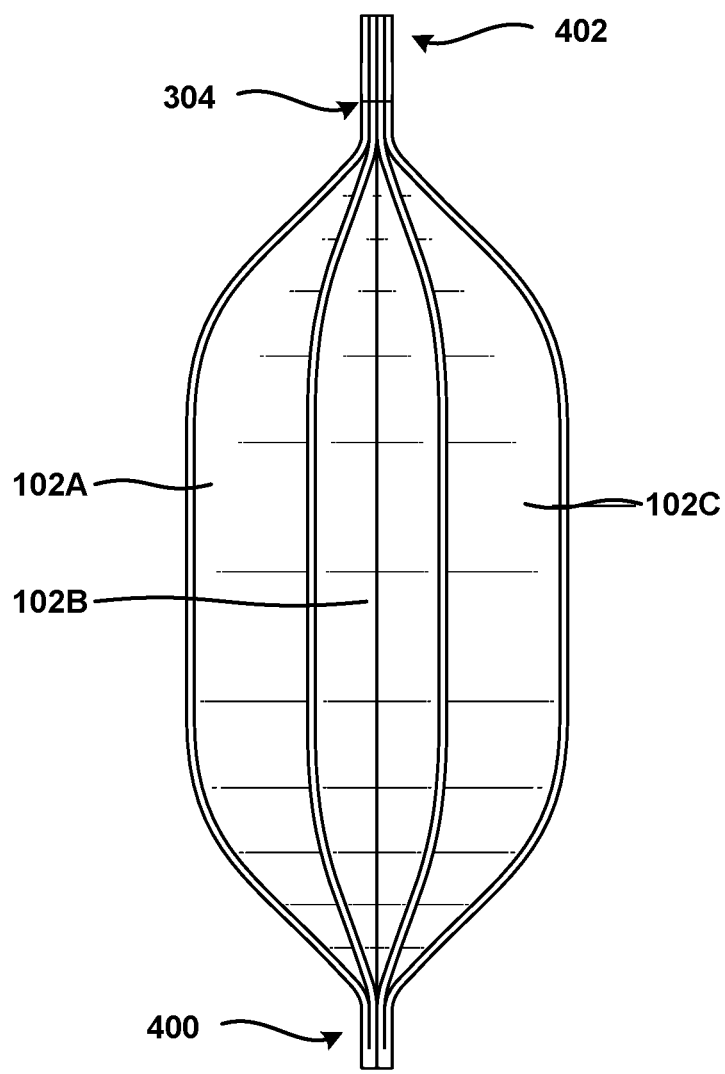
FIG. 4B is a line drawing showing a top elevation view of a selectively opening multiple compartment package, according to some other illustrative embodiments of the concepts and technologies disclosed herein.
Figure 4C:
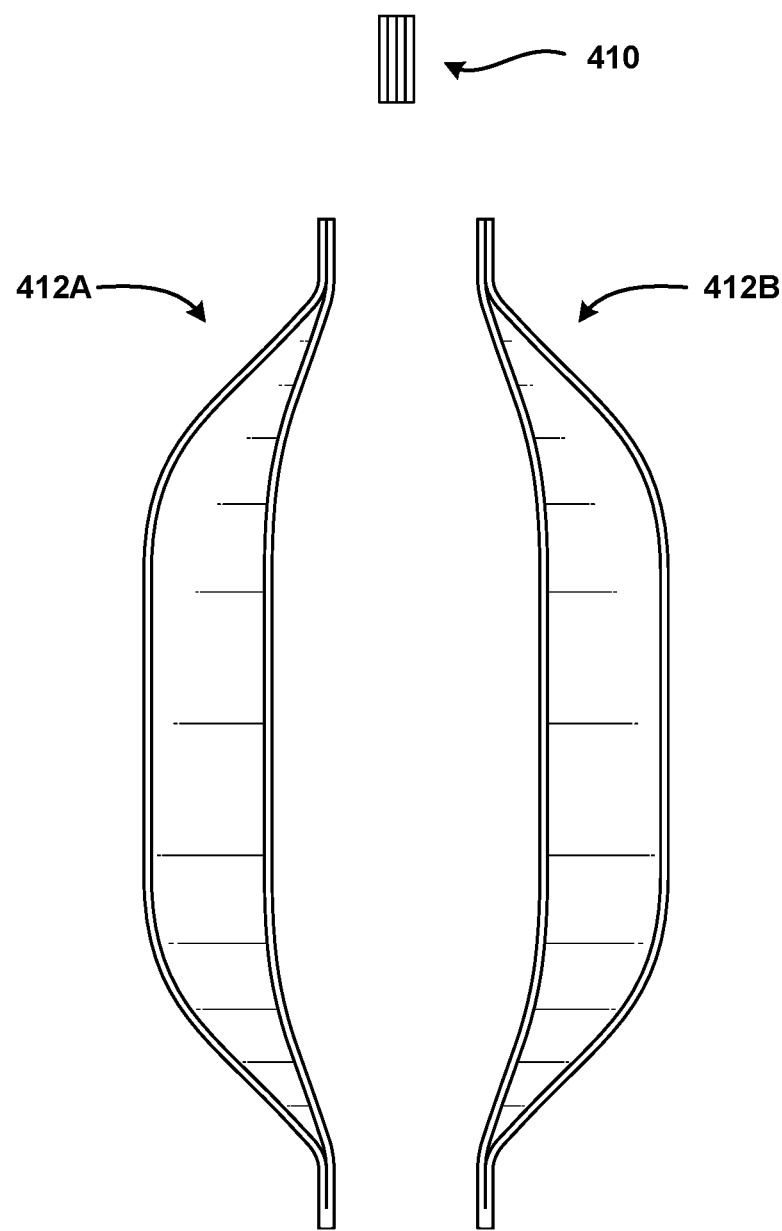
FIG. 4C is a line drawing showing a top elevation view of a selectively opening multiple compartment package with the tear away portion separated therefrom, according to some illustrative embodiments of the concepts and technologies disclosed herein.

The blank 200B can be folded again along the fold line 204B, as shown in FIG. 3F, thereby obtaining three compartments 102 of the selectively opening multiple compartment package 100. In some embodiments, a compression seal, a heat seal, an adhesive, or other sealing mechanism(s) (hereinafter collectively and/or generically referred to as an "additional compartment seal") 302 can be applied to crimp or seal the remaining edges, as shown in FIG. 3G. According to various embodiments, including the embodiment shown in FIG. 3G, the perforations 210 of the blank 200B can align to form a tear line 304 in the selectively opening multiple compartment package 100. The use of this tear line 304 will be illustrated and described in more detail with reference to top views of the selectively opening multiple compartment package 100 as shown in FIGS. 4B-4C. It should be understood that this example is illustrative, and therefore should not be construed as being limiting in any way.

Although the tear line 304 can be formed, in some embodiments, by folding the blank 200B, it also should be understood that the tear line 304 can be formed in alternative manners (e.g., from the blank 200A). In particular, the blank 200A can be folded using folding and sealing operations as illustrated and described with reference to FIGS. 3D-3G, and a perforation to function as the tear line 304 can be formed through the panels 202 (instead of aligning the perforations 210). Thus, it can be appreciated that the various embodiments of the selectively opening multiple compartment package 100 illustrated and described herein can be formed from the blank 200A and/or other blanks.

It can be appreciated with reference to the FIG. 2A and FIGS. 3A-3C that each of the panels 202 can provide a layer of material for the selectively opening multiple compartment package 100. In particular, the panel 202A can have a first side 302A and a second side 302B. Similarly, the panel 202B can have a first side 304A and a second side 304B. Still further, the panel 202C can have a first side 306A and a second side 306B. Finally (final only in the four panel 202 version of the selectively opening multiple compartment package 100), the panel 202D can have a first side 308A and a second side 308B. Thus, as can be appreciated with reference to FIGS. 1A-3C, the compartments 102 of the selectively opening multiple compartment package 100 can be formed and/or bound as follows. The first compartment 102A can be bound by a second side 302B of the panel 202A and the first side 304A of the panel 202B. It therefore can be appreciated that the first side 302A of the panel 202A can provide a front layer (i.e., the front surface 104) of the selectively opening multiple compartment package 100. Similarly, the panel 202B can provide the functionality of a first divider of the selectively opening multiple compartment package 100.

The second compartment 102B can be bound by a second side 304B of the panel 202B and the first side 306A of the panel 202C. It therefore can be appreciated that the panel 202C can provide the functionality of a second divider of the selectively opening multiple compartment package 100. Similarly, the third compartment 102C can be bound by a second side 306B of the panel 202C and the first side 308A of the panel 202D. It therefore can be appreciated that the second side 308B of the panel 202D can provide a rear layer (i.e., the rear surface 106) of the selectively opening multiple compartment package 100. A seal can be located between layers of each of the compartments 102, as illustrated and described herein. Thus, as used in the claims, a "layer" can correspond to a layer of material such as a panel 202. It should be understood that this example is illustrative, and therefore should not be construed as being limiting in any way.

Turning now to FIGS. 4A-4C, additional aspects of the selectively opening multiple compartment package 100 will be described. In particular, as noted above, FIG. 4A is a line drawing showing a top elevation view of the selectively opening multiple compartment package 100, according to some embodiments of the concepts and technologies disclosed herein. In the example embodiment shown in FIG. 4A, the selectively opening multiple compartment package 100 can be obtained by folding and sealing a blank such as the blank 200A illustrated and described with reference to FIG. 2A. In some embodiments, the folding and sealing of the blank 200A can be similar or even identical to the folding and sealing operations illustrated and described with reference to FIGS. 3A-3C. It should be understood that this example is illustrative, and therefore should not be construed as being limiting in any way.

As shown in FIG. 4A, the selectively opening multiple compartment package 100 can have three compartments that can converge at a first sealed end 400 and a second sealed end 402. According to various embodiments, the first sealed end 400 and the second sealed end 402 can be formed by sealing together the panels 202 as illustrated and described with reference to FIGS. 2A and 3A-3C. According to some embodiments, the first sealed end 400 and a second sealed end 402 can be sealed using the same sealing technique (e.g., heat, compression, mechanical manipulation such as crimping or the like, adhesives, etc.). According to some other embodiments, the first sealed end 400 can be sealed using a first sealing technique and the second sealed end 402 can be sealed using a second sealing technique. According to various embodiments, three sides or edges (e.g., the first side edge 112, the second side edge 114, and the bottom edge 108) are sealed using a first sealing technique that is permanent, and the fourth side or edge (e.g., the top edge 110) is sealed using an adhesive to enable a user or other entity to peel open only one compartment 102 at a time. Because selectively opening compartments 102 can be formed and/or sealed in additional and/or alternative manners, it should be understood that this example is illustrative, and therefore should not be construed as being limiting in any way.

As shown in FIG. 4A, the thickness of the selectively opening multiple compartment package 100 can be less at the first sealed end 400 than at another portion of the selectively opening multiple compartment package 100 (e.g., at a center portion about half way between the first sealed end 400 and the second sealed end 402). It should be understood that this example is illustrative, and therefore should not be construed as being limiting in any way.

FIG. 4B is a line drawing showing a top elevation view of the selectively opening multiple compartment package 100, according to some other embodiments of the concepts and technologies disclosed herein. In the example embodiment shown in FIG. 4B, the selectively opening multiple compartment package 100 can be obtained by folding and sealing a blank such as the blank 200B illustrated and described with reference to FIG. 2B. In some embodiments, the folding and sealing of the blank 200B can be similar or even identical to the folding and sealing operations illustrated and described with reference to FIGS. 3D-3G. It should be understood that this example is illustrative, and therefore should not be construed as being limiting in any way.

As shown in FIG. 4B, the selectively opening multiple compartment package 100 can have three compartments that can converge at a first sealed end 400 and a second sealed end 402, and the sealing of the first sealed end 400 and/or second sealed end 402 can be substantially similar to the sealing illustrated and described with reference to FIG. 4A. Additionally, as can be appreciated with reference to FIGS. 2B and 3D-3G, the perforations 210 of the blank 200B can align to provide the tear line 304 as explained above with reference to FIG. 3G. Thus, the multiple panels 202 of the blank 200B can be torn, if desired, substantially simultaneously by tearing along the aligned perforations 210, which can collectively provide the tear line 304.

This is illustrated in FIG. 4C, wherein the tear away portion 410 of the selectively opening multiple compartment package 100 is illustrated as having been separated from the selectively opening multiple compartment package 100. In various embodiments, the tear away portion 410 can be removed by tearing along the tear line 304 as illustrated and described above. It should be understood that this example is illustrative, and therefore should not be construed as being limiting in any way.

According to various embodiments, the compartments 102A and 102C can have an additional seal 302 (as illustrated and described above with reference to FIGS. 3D-3G). Thus, after removing the tear away portion 410 of the selectively opening multiple compartment package 100, the selectively opening multiple compartment package 100 can be separated into two single compartment storage packages 412A-B (hereinafter collectively and/or generically referred to as "single compartment storage packages 412"). Thus, for example, a user or other entity may use one or more items housed within the selectively opening multiple compartment package 100 and then separate and/or keep one or more single compartment storage packages 412. It should be understood that this example is illustrative, and therefore should not be construed as being limiting in any way.

Figure 5:
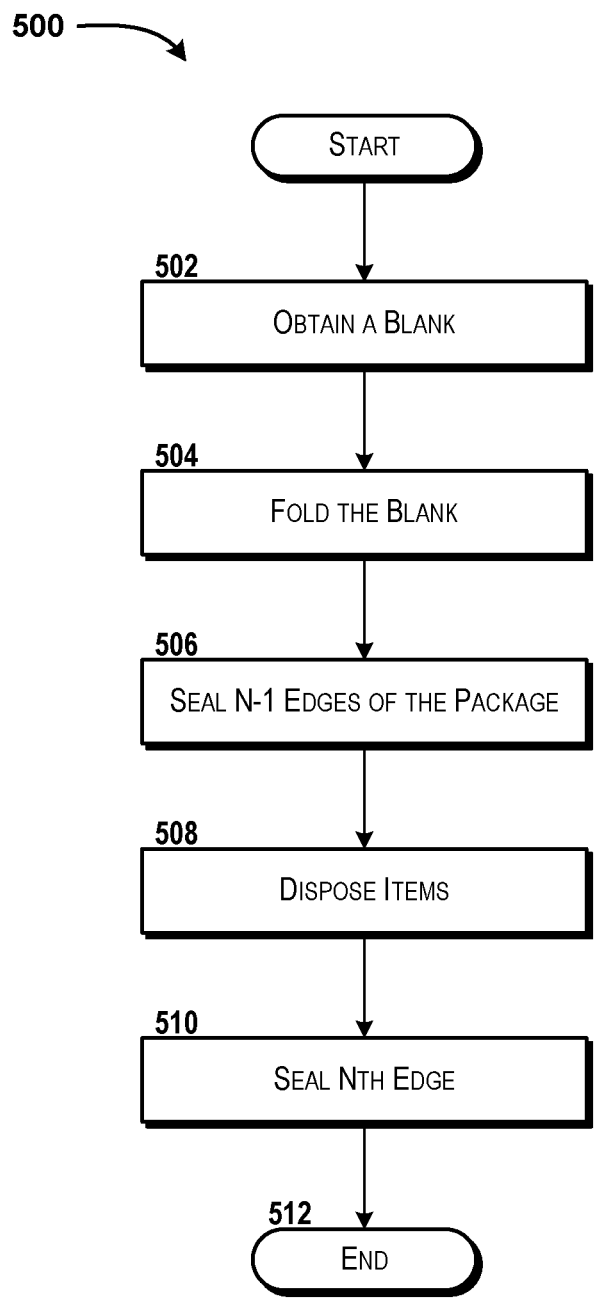
FIG. 5 is a flow diagram showing aspects of a method for making selectively opening multiple compartment packages, according to an illustrative embodiment of the concepts and technologies described herein.

Turning now to FIG. 5, aspects of a method 500 for making selectively opening multiple compartment packages will be described in detail, according to an illustrative embodiment of the concepts and technologies disclosed herein. It should be understood that the operations of the methods disclosed herein are not necessarily presented in any particular order and that performance of some or all of the operations in an alternative order(s) is possible and is contemplated. The operations have been presented in the demonstrated order for ease of description and illustration. Operations may be added, omitted, and/or performed simultaneously, without departing from the scope of the concepts and technologies disclosed herein.

It also should be understood that all methods disclosed herein can be ended at any time and need not be performed in their entireties. Some or all operations of the methods, and/or substantially equivalent operations, can be performed by execution of computer-readable instructions included on a computer storage media, as defined herein. The term "computer-readable instructions," and variants thereof, as used herein, is used expansively to include routines, applications, application modules, program modules, programs, components, data structures, algorithms, and the like. Computer-readable instructions can be implemented on various system configurations including single-processor or multi-processor systems, minicomputers, mainframe computers, personal computers, hand-held computing devices, microprocessor-based, programmable consumer electronics, combinations thereof, and the like.

Thus, it should be appreciated that the logical operations described herein are implemented (1) as a sequence of computer implemented acts or program modules running on a computing system or other device and/or (2) as interconnected machine logic circuits or circuit modules within the computing system. The implementation is a matter of choice dependent on the performance and other requirements of the computing system. Accordingly, the logical operations described herein are referred to variously as states, operations, structural devices, acts, or modules. These states, operations, structural devices, acts, and modules may be implemented in software, in firmware, in special purpose digital logic, and any combination thereof. As used herein, the phrase "cause a processor to perform operations" and variants thereof is used to refer to causing a processor of a computing system or device, such as a package forming device or a computing device that controls one or more package forming devices (e.g., devices included in an assembly line), to perform one or more operations and/or causing the processor to direct other components of the computing system or device to perform one or more of the operations.

For purposes of illustrating and describing the concepts of the present disclosure, the method 500 is described herein as being performed by a package forming device via execution of one or more software modules such as, for example, a selectively opening multiple compartment package forming application. It should be understood that additional and/or alternative devices can provide the functionality described herein via execution of one or more modules, applications, and/or other software including, but not limited to, the selectively opening multiple compartment package forming application, CNC programs, or the like. Thus, the illustrated embodiments are illustrative, and should not be viewed as being limiting in any way.

The method 500 begins at operation 502. At operation 502, the package forming device can obtain a blank of material such as, for example, the blank 200A illustrated and described herein with reference to FIG. 2A. In some embodiments, the blanks obtained in operation 502 can be provided to the package forming device (e.g., on a conveyor belt or other supply device), while in some other embodiments, the package forming device can form the blank in operation 502 (e.g., by cutting a sized portion of material from a larger piece of material). In one contemplated embodiment, a roll of laminated foil or other material as illustrated and described herein can be cut, by the package forming device, to a desired size to form the blank in operation 502. It should be understood that this example is illustrative, and therefore should not be construed as being limiting in any way.

From operation 502, the method 500 can proceed to operation 504. At operation 504, the package forming device can fold the blank obtained in operation 502. In various embodiments of the concepts and technologies disclosed herein, the blank obtained in operation 502 can be folded N times (where N is one less than the number of panels 202 included in the blank). In one contemplated embodiment, the blank obtained in operation 502 can be similar to the blank shown in FIG. 2A and therefore can have four panels 202 and can be folded three (four minus one) times to form a W-shaped or M-shaped piece of material (as shown in FIGS. 3A-3G). According to various embodiments of the concepts and technologies disclosed herein, the blank can be folded on fold lines, though in many embodiments of the concepts and technologies disclosed herein, the blank does not have fold lines formed therein. Rather, the fold lines shown in the drawings are provided for purposes of clarity. It should be understood that this example is illustrative, and therefore should not be construed as being limiting in any way.

From operation 504, the method 500 can proceed to operation 506. At operation 506, the package forming device can seal N−1 edges (where N is the total number of edges) of the blank obtained in operation 502 and folded in operation 504. In some embodiments, the selectively opening multiple compartment package 100 is configured to have four edges (as shown in FIGS. 1A-1B) and therefore three edges can be sealed in operation 506. Thus, in operation 506 an open version of the selectively opening multiple compartment package 100 as shown in FIG. 1B can be obtained. As noted above, the selectively opening multiple compartment package 100 can have more than three edges and more than three compartments 102, so the example shown in FIG. 1B with three edges and three compartments 102 is illustrative. It should be understood that this example is illustrative, and therefore should not be construed as being limiting in any way.

From operation 506, the method 500 can proceed to operation 508. At operation 508, the package forming device can dispose items into the compartments 102 of the open version of the selectively opening multiple compartment package 100 as obtained in operation 506. As noted above, any desired items can be loaded into the open version of the selectively opening multiple compartment package 100. In one contemplated embodiment, a condom can be located in one of the compartments 102 and two other items can be located in the remaining two (or more) compartments 102.

From operation 508, the method 500 can proceed to operation 510. At operation 510, the package forming device can seal the nth edge of the selectively opening multiple compartment package 100, thereby forming the sealed version of the selectively opening multiple compartment package 100. From operation 510, the method 500 can proceed to operation 512. The method 500 can end at operation 512.

Figure 6:
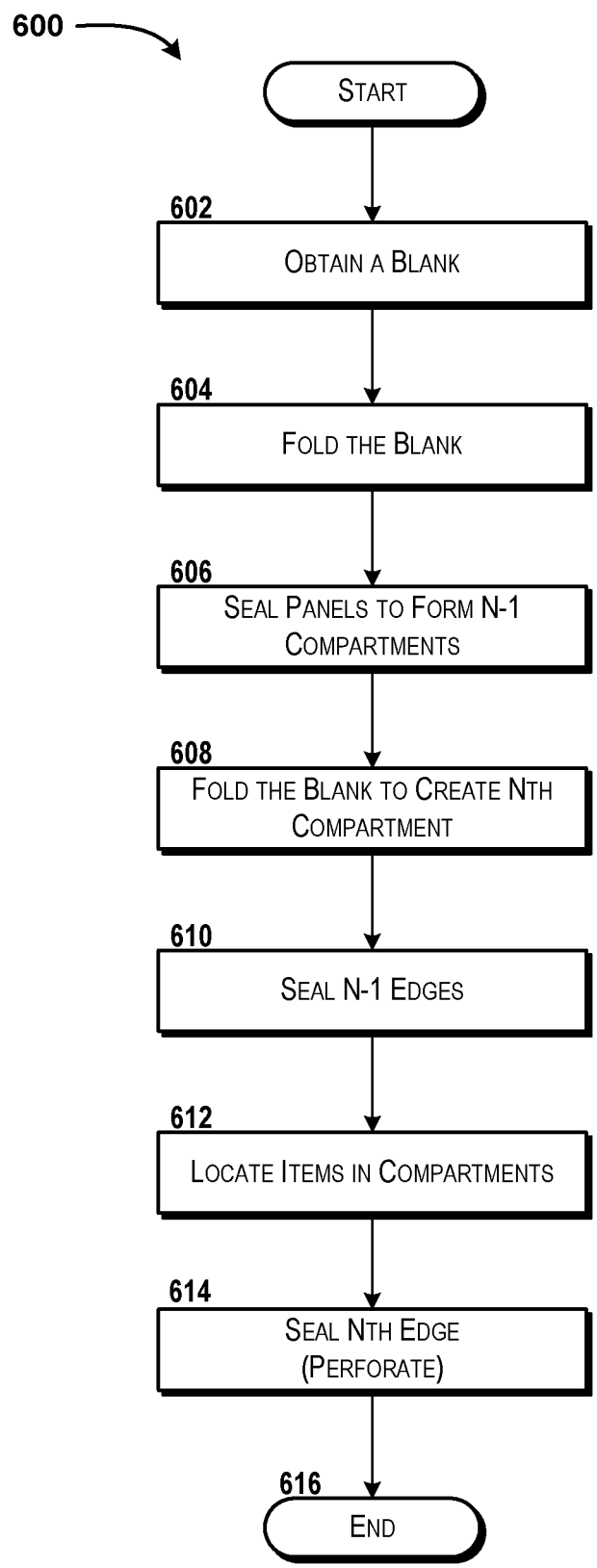
FIG. 6 is a flow diagram showing aspects of a method for making selectively opening multiple compartment packages, according to another illustrative embodiment of the concepts and technologies described herein.

Turning now to FIG. 6, aspects of a method 600 for making selectively opening multiple compartment packages will be described in detail, according to an illustrative embodiment. The method 600 begins at operation 602. At operation 602, the package forming device can obtain a blank of material such as, for example, the blanks 200A or 200B illustrated and described herein with reference to FIGS. 2A-2B. It should be understood that the operation 602 can be, but is not necessarily, similar or even identical to the operation 502 described above with regard to FIG. 5. As such, the blanks obtained in operation 602 can be provided to the package forming device or formed in operation 602. In some embodiments, the blank can be formed with perforations (e.g., the material can be perforated in addition to being cut in operation 602; or the perforations can be included in the blank obtained). The perforations can be, but are not necessarily, similar or even identical to the perforations 210 illustrated and described herein. It should be understood that this example is illustrative, and therefore should not be construed as being limiting in any way.

From operation 602, the method 600 can proceed to operation 604. At operation 604, the package forming device can fold the blank obtained in operation 602. In various embodiments of the concepts and technologies disclosed herein, the blank obtained in operation 602 can be folded N−1 times (where N is the total number of folds to be performed; one less than the number of panels 202 included in the blank and equal to the number of compartments 102 to be included in the selectively opening multiple compartment package 100). In one contemplated embodiment, the blank obtained in operation 602 can be similar to the blank shown in FIG. 2B and therefore can have four panels 202 and can be folded two (four minus two) times in operation 604 (as shown in FIG. 3D). As explained herein, the blank can be folded on fold lines 204, though in some embodiments of the concepts and technologies disclosed herein, the blank does not have fold lines 204 formed therein. It should be understood that this example is illustrative, and therefore should not be construed as being limiting in any way.

From operation 604, the method 600 can proceed to operation 606. At operation 606, the package forming device can seal the folded over panels 202 to form N−1 compartments 102 (where N is the total number of compartments 102 to be included in the selectively opening multiple compartment package 100). Thus, in operation 606, one or more compartments 102 can be formed. An example of this operation is illustrated and described above with reference to FIG. 3E. It should be understood that this example is illustrative, and therefore should not be construed as being limiting in any way.

From operation 606, the method 600 can proceed to operation 608. At operation 608, the package forming device can fold the blank an Nth time, where N is equal to the total number of folds and/or the total number of compartments 102 to be formed in the selectively opening multiple compartment package 100.

From operation 608, the method 600 can proceed to operation 610. At operation 610, the package forming device can seal N−1 edges (where N is the total number of edges of the selectively opening multiple compartment package 100). In some embodiments, the selectively opening multiple compartment package 100 is configured to have four edges (as shown in FIGS. 1A-1B) and therefore three edges can be sealed in operation 610. Thus, in operation 610 an open version of the selectively opening multiple compartment package 100 as shown in FIG. 1B can be obtained. As noted above, the selectively opening multiple compartment package 100 can have more than three edges and more than three compartments 102, so the example shown in FIG. 1B with three edges and three compartments 102 is illustrative. It should be understood that this example is illustrative, and therefore should not be construed as being limiting in any way.

From operation 610, the method 600 can proceed to operation 612. At operation 612, the package forming device can dispose or otherwise locate items into the compartments 102 of the open version of the selectively opening multiple compartment package 100 as obtained in operation 610. As noted above, any desired items can be loaded into the open version of the selectively opening multiple compartment package 100.

From operation 612, the method 600 can proceed to operation 614. At operation 614, the package forming device can optionally perforate one or more portions of the selectively opening multiple compartment package 100 and can seal the Nth edge of the selectively opening multiple compartment package 100, thereby forming the sealed version of the selectively opening multiple compartment package 100. As explained herein, the perforating of the selectively opening multiple compartment package 100 can be performed to create a tear line such as the tear line 304 illustrated and described herein (thereby enabling separation of the sealed compartments 102 of the selectively opening multiple compartment package 100 if desired). In some other embodiments, the blank obtained in operation 602 can include perforations such as the perforations 210 illustrated and described herein, and as such, perforation may not be performed in operation 614. As such, it should be understood that this example is illustrative, and therefore should not be construed as being limiting in any way.

From operation 614, the method 600 can proceed to operation 616. The method 600 can end at operation 616.

Based on the foregoing, it should be appreciated that concepts and technologies for selectively opening multiple compartment packages and methods for making selectively opening multiple compartment packages are provided herein. Although the subject matter presented herein has been described in language specific to structural features and methodological acts, it is to be understood that the invention defined in the appended claims is not necessarily limited to the specific features or acts described herein. Rather, the specific features and acts are disclosed as example forms of implementing the claims.

The subject matter described above is provided by way of illustration only and should not be construed as limiting. Various modifications and changes may be made to the subject matter described herein without following the example embodiments and applications illustrated and described, and without departing from the true spirit and scope of the present invention, which is set forth in the following claims.

The invention claimed is:

1. A selectively opening multiple compartment package comprising:
   a front layer comprising a first side of the front layer and a second side of the front layer;
   a first divider comprising a first side of the first divider and a second side of the first divider;
   a second divider comprising a first side of the second divider and a second side of the second divider;
   a rear layer comprising a first side of the rear layer and a second side of the rear layer;
   a first compartment bound by the second side of the front layer and the first side of the first divider;
   a second compartment bound by the second side of the first divider and the first side of the second divider;

a third compartment bound by the second side of the second divider and the first side of the rear layer, wherein the first side of the front layer and the second side of the rear layer comprise external surfaces of the selectively opening multiple compartment package, and wherein the first compartment, the second compartment, and the third compartment are configured to be selectively opened, wherein the front layer is formed from a first panel of a material blank, wherein the first divider is formed from a second panel of the material blank, wherein the second panel is located adjacent to the first panel on a first edge of the second panel and adjacent to a third panel of the material blank on a second edge of the second panel, wherein the second divider is formed from the third panel of the material blank, wherein the third panel is located adjacent to the second panel on a first edge of the third panel and adjacent to a fourth panel of the material blank on a second edge of the third panel, wherein the rear layer is formed from the fourth panel, wherein the second side of the front layer and the first side of the first divider are sealed together by a first heat seal, wherein the second side of the first divider and the first side of the second divider are sealed together by a second heat seal, wherein the second side of the second divider and the first side of the rear layer are sealed together by a third heat seal, and wherein the material blank is formed as a single piece of material; and a tear line, wherein tearing along the tear line enables separation of the first compartment from the second compartment and separation of the third compartment from the second compartment.

2. The selectively opening multiple compartment package of claim 1, wherein selectively opening comprises destroying only one heat seal of the first heat seal, the second heat seal, or the third heat seal.

3. The selectively opening multiple compartment package of claim 1, wherein the single piece of material is folded to form the first panel, the second panel, the third panel, and the fourth panel.

4. The selectively opening multiple compartment package of claim 1, further comprising a first item located in the first compartment, a second item that is different from the first item is located in the second compartment, and a third item that is different from the first item and the second item is located in the third compartment.

5. The selectively opening multiple compartment package of claim 1, wherein the selectively opening multiple compartment package is formed from a single unitary piece of laminated foil that is folded.

6. A selectively opening multiple compartment package comprising:
a front layer comprising a first side of the front layer and a second side of the front layer;
a first divider comprising a first side of the first divider and a second side of the first divider;
a second divider comprising a first side of the second divider and a second side of the second divider;
a rear layer comprising a first side of the rear layer and a second side of the rear layer;
a first compartment bound by the second side of the front layer and the first side of the first divider;
a second compartment bound by the second side of the first divider and the first side of the second divider;
a third compartment bound by the second side of the second divider and the first side of the rear layer, wherein the first side of the front layer and the second side of the rear layer comprise external surfaces of the selectively opening multiple compartment package, wherein the second compartment can be opened without opening the first compartment and without opening the third compartment, wherein the front layer is formed from a first panel of a material blank, wherein the first divider is formed from a second panel of the material blank, wherein the second panel is located adjacent to the first panel on a first edge of the second panel and adjacent to a third panel of the material blank on a second edge of the second panel, wherein the second divider is formed from the third panel of the material blank, wherein the third panel is located adjacent to the second panel on a first edge of the third panel and adjacent to a fourth panel of the material blank on a second edge of the third panel, wherein the rear layer is formed from the fourth panel, wherein the second side of the front layer and the first side of the first divider are sealed together by a first heat seal, wherein the second side of the first divider and the first side of the second divider are sealed together by a second heat seal, wherein the second side of the second divider and the first side of the rear layer are sealed together by a third heat seal, and wherein the material blank is formed as a single piece of material; and a tear line, wherein tearing along the tear line enables separation of the first compartment from the second compartment and separation of the third compartment from the second compartment.

7. The selectively opening multiple compartment package of claim 6, wherein selectively opening comprises destroying only one heat seal of the first heat seal, the second heat seal, or the third heat seal.

8. The selectively opening multiple compartment package of claim 6, wherein selectively opening comprises destroying only the second heat seal.

9. The selectively opening multiple compartment package of claim 6, wherein the single piece of material is folded to form the first panel, the second panel, the third panel, and the fourth panel.

10. The selectively opening multiple compartment package of claim 6, further comprising a first item located in the first compartment, a second item that is different from the first item is located in the second compartment, and a third item that is different from the first item and the second item is located in the third compartment.

11. The selectively opening multiple compartment package of claim 6, wherein the selectively opening multiple compartment package is formed from a single unitary piece of laminated foil that is folded.

12. A package comprising:
a front layer comprising a first side of the front layer and a second side of the front layer;
a first divider comprising a first side of the first divider and a second side of the first divider;
a second divider comprising a first side of the second divider and a second side of the second divider;
a rear layer comprising a first side of the rear layer and a second side of the rear layer, wherein a first compartment is formed by the second side of the front layer and the first side of the first divider, wherein a second compartment is formed by the second side of the first divider and the first side of the second divider, wherein a third compartment is formed by the second side of the second divider and the first side of the rear layer, wherein the first side of the front layer and the second side of the rear layer comprise external surfaces of the package, and wherein the first compartment, the second compartment, and the third compartment are configured to be selectively opened, wherein the front layer is formed from a first panel of a material blank, wherein the first divider is formed from a second panel of the material blank, wherein the second panel is located adjacent to the first panel on a first edge of the second panel and adjacent to a third panel of the material blank on a second edge of the second panel, wherein the second divider is formed from the third panel of the material blank, wherein the third panel is located adjacent to the second panel on a first edge of the third panel and adjacent to a fourth panel of the material blank on a second edge of the third panel, wherein the rear layer is formed from the fourth panel, wherein the second side of the front layer and the first side of the first divider are sealed together by a first heat seal, wherein the second side of the first divider and the first side of the second divider are sealed together by a second heat seal, wherein the second side of the second divider and the first side of the rear layer are sealed together by a third heat seal, and wherein the material blank is formed as a single piece of material; and a tear line, wherein tearing along the tear line enables separation of the first compartment from the second compartment and separation of the third compartment from the second compartment.

13. The package of claim 12, wherein selectively opening comprises destroying only one heat seal of the first heat seal, the second heat seal, or the third heat seal.

14. The package of claim 12, wherein the single piece of material is folded to form the first panel, the second panel, the third panel, and the fourth panel.

* * * * *